United States Patent [19]

Manimaran et al.

[11] Patent Number: 5,248,813
[45] Date of Patent: Sep. 28, 1993

[54] ENANTIOMERIC RESOLUTION

[75] Inventors: Thanikavelu Manimaran; G. Patrick Stahly; R. Carl Herndon, Jr., all of Baton Rouge, La.

[73] Assignee: Ethyl Corporation, Richmond, Va.

[21] Appl. No.: 960,660

[22] Filed: Oct. 14, 1992

[51] Int. Cl.$^5$ ............................................. C07B 57/00
[52] U.S. Cl. ..................................... 562/401; 556/114; 556/131; 558/414; 560/21; 560/23; 560/38; 560/39; 560/43; 560/44; 560/56; 560/59; 560/60; 560/61; 560/62; 560/100; 560/103
[58] Field of Search ...................... 562/401; 560/21, 23, 560/38, 39, 43, 44, 56, 57, 60, 61, 62, 100, 103; 558/414; 556/114, 131

[56] References Cited

U.S. PATENT DOCUMENTS

| | | | |
|---|---|---|---|
| 4,831,147 | 5/1989 | Russell | 546/302 |
| 4,865,770 | 9/1989 | Piselli | 562/402 |
| 4,931,587 | 6/1990 | Piselli | 562/401 |
| 4,973,745 | 11/1990 | Blaschke et al. | 562/401 |

OTHER PUBLICATIONS

Collet et al., *Chem. Rev.* 80(3), pp. 215-230 (1980).
Jaques et al., *Enantiomers, Racemates and Resolutions*, Chapter 3, J. Wiley & Sons, New York, N.Y., (1981) pp. 167-213.
Collet, A., pp. 91-110 *Problems and Wonders of Chiral Molecules*, Simonyi, M. (Ed.), Akademai Keado, Budapest (1990).

*Primary Examiner*—José G. Dees
*Assistant Examiner*—Vera C. Clarke
*Attorney, Agent, or Firm*—Richard J. Hammond

[57] ABSTRACT

A process for obtaining a substantially pure enantiomer of an aryl-substituted aliphatic carboxylic acid is described. The process utilizes first an enantiomerically enriched mixture the of aryl-substituted aliphatic carboxylic acid obtained from kinetic resolution, diastereomeric crystallization or asymmetric synthesis processes. This enriched mixture is reacted with a base producing a salt that has the following properties:
(1) has at least one eutectic point;
(2) a composition that is not at the eutectic point; and
(3) a eutectic composition that is closer to the racemic composition than is the eutectic composition of said aryl-substituted carboxylic acid.

Substantially pure, enantiomeric salt is separated, leaving a mother liquor comprising the solvent and aryl-substituted aliphatic carboxylic acid enriched in the other enantiomer.

16 Claims, No Drawings

ENANTIOMERIC RESOLUTION

FIELD OF INVENTION

This invention relates to a process for obtaining highly pure enantiomers of aryl-substituted carboxylic acids from a mixture of enantiomers.

BACKGROUND OF INVENTION

The resolution of racemates constitutes the main method for industrial preparation of pure enantiomers. Methods for such resolution include: direct preferential crystallization; crystallization of the diastereomeric salts and kinetic resolution. Pure enantiomers may also be produced by asymmetric synthesis (reaction of a chiral auxiliary or catalyst with a prochiral substrate).

Also referred to as resolution by entrainment, preferential crystallization is widely used on an industrial scale; for example, in the manufacture of α-methyl-L-dopa and chloramphenicol. It is technically feasible only with racemates which are so-called conglomerates and consist of mechanical mixtures of crystals of the two enantiomers. Unfortunately, less than 20 percent of all racemates are conglomerates. The rest are true racemic compounds which cannot be separated by preferential crystallization (e.g., by seeding a saturated solution of the racemate with the crystals of one enantiomer). A conglomerate exhibits a minimum melting point for the racemic composition while a racemic compound does not. Further, a conglomerate is generally viewed as an equimolar mixture of two crystalline enantiomers that are, in principle, mechanically separable. Its phase diagram, i.e. a plot of the melting point versus the enantiomeric composition, displays one sharply defined minimum temperature at a mixture of 50% and 50% which is the eutectic point of the enantiomeric mixture. The success of preferential crystallization depends on the fact that the solubility of the pure enantiomer is less than the solubility of the racemic composition, i.e., the mixture having the lowest melting point is the racemic mixture which is most soluble. For a conglomerate, this is the racemic mixture.

If the racemate is a true racemic compound, a homogeneous solid phase of the two enantiomers co-exists in the same unit cell. These materials may be separated via diastereomer crystallization, which generally involves reaction of the racemate with an optically pure acid or base (the resolving agent) to form a mixture of diastereomeric salts which are then separated by crystallization. Ibuprofen, for example, is a true racemic compound.

Diastereomer crystallization is widely used for the industrial synthesis of pure enantiomers. A typical example is the Andeno process for the manufacture of (D)-(−)-phenylglycine, an antibiotic intermediate, using optically pure camphor sulfonic acid as the resolving agent. Also see U.S. Pat. No. 4,752,417 for a diastereomeric procedure for resolving certain phenylacetic acid derivatives and U.S. Pat. No. 4,973,745 for resolving 2-arylpropionic acids.

The theoretical once-through yield of a resolution via diastereomer crystallization is 50 percent. However, in practice, a single recrystallization produces a composition that is simply an enantiomerically enriched racemate.

Another method for the resolution of racemates is kinetic resolution, the success of which depends on the fact that the two enantiomers react at different rates with a chiral addend.

Kinetic resolution can also be effected using chiral metal complexes as chemocatalysts, e.g., the enantioselective rhodium-BINAP-catalyzed isomerization of chiral allylic alcohols to the analogous prostaglandin intermediates reported by Noyori.

The enantioselective conversion of a prochiral substrate to an optically active product, by reaction with a chiral addend, is referred to as an asymmetric synthesis. From an economic viewpoint, the chiral addend functions in catalytic quantities. This may involve a simple chemocatalyst or a biocatalyst. An example of the former is the well-known Monsanto process for the manufacture of L-dopa by catalytic asymmetric hydrogenation. See Knowles, et al., *J. Am. Chem. Soc.*, 97, 2567 (1975). An example of the latter is the Genex process for the synthesis of L-phenylalanine by the addition of ammonia to transcinnamic acid in the presence of L-phenylalanine ammonia lyase (PAL). See Hamilton et al., *Trends in Biotechnology*, 3, 64–68, (1985). Also see Jacques et al., *Enantiomers, Racemates and Resolutions*, Chapter 3 (1981) incorporated herein by reference.

With the exception of the preferential crystallization process when applied to true conglomerates, the prior art processes typically produce a first mixture that is essentially an enantiomerically enriched racemic composition. A number of crystallizations are required to yield the substantially pure enantiomer.

OBJECTS OF THE INVENTION

It is an object of the present invention to provide a process for obtaining a substantially pure enantiomer of an aryl-substituted aliphatic carboxylic acid or the ester thereof.

It is a further object of the present invention to obtain such a substantially pure enantiomer from a composition of enantiomerically enriched aryl-substituted aliphatic carboxylic acid.

PREFERRED EMBODIMENTS OF THE INVENTION

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3-tetramethylbutyl, nonyl, decyl, dodecyl, tetradecyl, hexadecyl, octadecyl and eicosyl;

cycloalkyl means cyclic alkyl having 3 to 7 carbon atoms and includes cyclopropyl, cyclobutyl, cyclopentyl, cyclohexyl and cycloheptyl;

substituted phenyl or substituted naphthyl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

haloalkyl means straight or branched chain alkyl having 1 to 10 carbon atoms which is substituted at least one halogen as mentioned above;

hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1-hydroxy-2-propyl, 2-hydroxypropyl, 2,3-dihydroxypropyl, 1,3-dihydroxy-2-propyl;

alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl 6-oxtyloxyhexyl, 8-methoxyoctyl, 8-ethoxyoctyl, 8-butoxyoctyl, 8-hexyloxyoctyl and 8-octyloxyoctyl;

acyloxyalkyl means that the acyl moiety is alkanoyl having 2 to 18 carbon atoms, benzoyl, substituted benzoyl, heteroarylcarbonyl or substituted heteroarylcarbonyl and the alkyl moiety is straight or branched chain alkyl having 1 to 8 carbon atoms, and includes, for example, acetoxymethyl, 2-acetoxyethyl, 3-acetoxypropyl, 4-acetoxybutyl, 6-acetoxyhexyl, 8-acetoxyoctyl, propionyloxymethyl, 2-propionyloxyethyl, 3-propionyloxypropyl, 4-propionyloxybutyl, 6-propionyloxyhexyl, 8-propionyloxyoctyl, isobutyryloxymethyl, 2-isobutyryloxyethyl, 4-isobutyryloxybutyl, pivaloyloxymethyl, 2-pivaloyloxyethyl, 4-pivaloyloxybutyl, butyryloxymethyl, 2-butyryloxyethyl, 4-butyryloxybutyl, valeryloxymethyl, 2-valeryloxyethyl, 4-valeryloxybutyl, hexanoyloxymethyl, 2-hexanoyloxyethyl, 4-hexanoyloxybutyl, octanoyloxymethyl, 2-octanoyloxyethyl, 4-octanoyloxybutyl, lauroyloxymethyl, 2-lauroyloxyethyl, 4-lauroyloxybutyl, stearoyloxymethyl, 2-stearoyloxyethyl, 4-stearoyloxybutyl, benzoyloxymethyl, 2-benzoyloxyethyl, 4-benzoyloxybutyl, furoyloxymethyl, 2-furoyloxyethyl, 4-furoyloxybutyl, thenoyloxymethyl, 2-thenoyloxyethyl, 4-thenoyloxybutyl, nicotinoyloxymethyl, 2-nicotinoyloxyethyl and 4-nicotinoyloxybutyl;

carboxyalkyl means that the alkyl moiety is straight or branched chain alkyl having 1 to 8 carbon atoms and includes , for example, carboxymethyl, 2-carboxymethyl, 3-carboxypropyl, 4-carboxybutyl, 6-carboxyhexyl and 8-carboxyoctyl;

alkoxycarbonylalkyl means that the alkoxy moiety and the alkyl moiety each are straight or branched chain ones having 1 to 8 carbon atoms, and includes, for example, methoxycarbonylmethyl, ethoxycarbonylmethyl, propoxycarbonylmethyl, isopropoxycarbonylmethyl, butoxycarbonylmethyl, isobutoxycarbonylmethyl, tertiary butoxycarbonylmethyl, pentlyoxycarbonylmethyl, hexyloxycarbonylmethyl, octyloxycarbonylmethyl, 2-methoxycarbonylethyl, 2-ethoxycarbonylethyl, 2-propoxycarbonylethyl, 2-butoxycarbonylethyl, 3-methoxycarbonylpropyl, 3-ethoxycarbonylpropyl, 3-propoxycarbonylpropyl, 3-butoxycarbonylpropyl, 4-methoxycarbonylbutyl, 4-ethoxycarbonylbutyl, 4-propoxycarbonylbutyl, 4-butoxycarbonylbutyl, 6-methoxycarbonylhexyl, 6-ethoxycarbonylhexyl, 8-methoxycarbonyloctyl and 8-ethoxycarbonyloctyl;

cyanoalkyl means that the alkyl moiety is straight or branched chain alkyl having 1 to 8 carbon atoms and includes, for example, cyanomethyl, 2-cyanoethyl, 3-cyanopropyl, 4-cyanobutyl, 6-cyanohexyl and 8-cyanooctyl; and The objective of the present invention is achieved by starting with an enantiomerically enriched mixture of an aryl-substituted aliphatic carboxylic acid or the ester thereof in an inert solvent. These materials have the following formula:

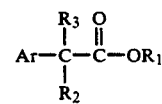

where $R_1$ is hydrogen or $C_1$ to $C_6$ linear or branched alkyl, $R_2$, and $R_3$ are hydrogen, alkyl, cycloalkyl, phenyl, substituted phenyl, naphthyl, substituted naphthyl, haloalkyl, hydroxyalkyl, alkoxyalkyl, acyloxyalkyl, carboxyalkyl, alkoxycarbonylalkyl or cyanoalkyl.

Ar is phenyl, substituted phenyl, naphthyl or substituted naphthyl.

Preferred compounds of Formula I are those of the formula:

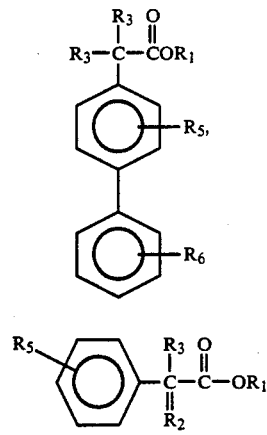

and

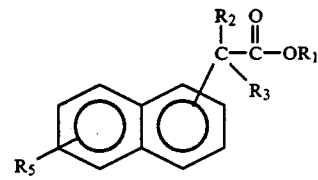

where $R_1$, and $R_2$ and $R_3$ are as previously defined and $R_5$ and $R_6$ are alkyl, alkoxy, acyloxyalkyl, or halo.

The process of the present invention is particularly applicable to 2-(4-isobutylphenyl)propionic acid and especially in obtaining a preponderance of the S(+)isomer.

The invention is carried out by using a mixture of both the (+) and (−) (or dextro and levo rotatory forms) containing a preponderance of one of the enantiomers of the carboxylic acids of formula I. However, it should be understood that the process itself does not convert one form of the stereoisomers to the other form but only separates such forms. Further in the preferred embodiment of this invention, the separation of enantiomers gives rise to a soluble product largely containing one enantiomer and an insoluble product largely containing the other enantiomer. As such, a high purity product is obtained that requires a minimum number of recrystallizations (usually not more than two) to give a product with exceptionally high optical purity.

The first step in the reaction sequence for the separation of the enriched mixtures used in the present invention is to form a salt of the aliphatic carboxylic acid of formula I with an optically inactive organic or inorganic base. When such base is an inorganic one, it is preferred that it is a metallic or ammonium hydroxide, carbonate, bicarbonate or chloride. The metal may be any metal. Metals in Group I or II of the Periodic Table of Elements are preferred. Most preferably, the metal of the inorganic base is from Group IA. Especially preferred is sodium hydroxide.

When the base used in the first step of the separation process is an optically inactive organic base, then it is preferably an aliphatic, aromatic or mixed aliphatic and aromatic amine. The only criteria for such optically inactive organic base is that it take part in no other reaction with the aliphatic carboxylic acid except salt formation and that it be soluble in the solution first used in the process of the present invention. Preferred organic bases are the substituted $C_1$ to $C_6$ linear or branched alkyl, phenyl, naphthyl, substituted phenyl or substituted naphthyl, amines such as propylamine, octylamine, butylamine racemic alpha-methylbenzylamine and the like.

The amount of base added to the carboxylic acid may be less than, equal to or more than the molar amounts of the carboxylic acid of formula I. However, it is preferred that the base have a ratio of from about 0.15 to about 0.95 mole per mole of carboxylic acids of formula I, most preferably from about 0.2 to 0.6 mole per mole of enantiomerically enriched aryl-substituted aliphatic carboxylic acid of formula I.

As a second step in the reaction sequence, an inert solvent is added. The solvent should be inert to the starting materials and the products. Conveniently, with the proper selection of solvents, a solid crystalline material will precipitate from the reaction mixture.

Any solvent that is not reactive with these carboxylic acids or esters is acceptable. Thus, various aliphatic hydrocarbon solvents, i.e., hexane, heptane, octane, etc., aromatic hydrocarbon solvents, i.e., benzene, toluene, xylene, alcohol solvents, i.e., methanol, ethanol, 1-propyl alcohol, etc., and water are preferred for such solvent. Particularly preferred are the aliphatic hydrocarbon solvents, especially hexane. It should be understood that mixtures of such solvents are also encompassed within the meaning of "inert solvent".

At this point in the reaction sequence (after the admixture of the solvent with the base and the enriched aryl-substituted aliphatic carboxylic acid or ester thereof), the salt and solvent may be heated, e.g. to a temperature of about 25° C. to about 125° C., preferably about 75° C. to 120° C., or the heating can occur before the salt solution is formed. Heating is typically carried out from about 1 to about 16 hours, preferably from about 2 to about 8 hours.

It is preferred that the solvent, base, aliphatic carboxylic acid to base stoichiometry and temperature are selected so that the number of moles of salt precipitating is less than the number of moles of enriched carboxylic acid initially charged.

Each of the salts formed from the reaction of optically inactive organic or inorganic base with aliphatic carboxylic acids of formula I exhibits a unique solubility phase diagram, i.e. a plot of the solubility versus enantiomeric composition.

The eutectic point in such phase diagrams represents the most soluble composition of the mixture of enantiomers. If a solid enriched mixture of enantiomers is admixed with a solvent, either all or part of the mixture will dissolve. If a sufficient amount of solvent is added so that the entire mixture becomes a solution, then cooling the solution (or evaporating some of the solvent or adding a nonsolvent, or any other conventional method used to precipitate solutes from solutions) will precipitate a portion of the salt. Depending on where the eutectic point lies the precipitated salt may be more highly enriched in one of the enantiomers or it may approach the composition of the racemic mixture. If the latter case occurs, obviously, the mother liquor will be more highly enriched than the initial aliphatic carboxylic acid enriched with one of the enantiomers.

Thus, the substantially pure salt formed from the enriched mixtures of compounds of formula I must have the following properties:

(i) at least one eutectic point;

(ii) a composition that is not at the eutectic point; and (iii) a eutectic composition that is closer to the racemic composition than it is to the eutectic composition of the the compounds represented by formula I.

In the phase diagram then, if the eutectic point is at the racemic composition, an enantiomeric mixture of 70% S(+) [and 30% R(−)] upon cooling preferentially forms the most soluble fraction of 50% S(+) and 50% R(−) [the racemic composition]. The precipitated product will then have a higher concentration of S(+) than the starting composition.

Conversely, where the starting enantiomeric enriched mixture is 30% S(+) [and 70% R(−)], the precipitated product will have a higher concentration of the R(−) enantiomer. It is less soluble than the racemic mixture which preferentially forms.

While the term "precipitated product" (or salt) is used in various places throughout this specification, it should be noted that a similar purification can occur by adding smaller amounts of solvent than would be required to completely dissolve the enriched salt. This preferential leaching or extraction process produces identical results as precipitation from solutions.

The crystalline residue separated in the above step is substantially pure enantiomeric material. However, it should be understood that the actual purity of such "substantially pure enantiomer" is dependent on the composition of the starting enantiomerically enriched carboxylic acid. Thus, by carrying out the process of this invention using a carboxylic acid of formula I having an optical purity of 66% ee (% ee equals the weight percent of major enantiomer minus the weight percent of minor enantiomer), the process of this invention yields the substantially pure enantiomeric salt, i.e., an 84% ee S(+) pure product. Compositions of greater enrichment in, for example, the S(+) isomer yield final product of even higher purity, i.e., an 76% ee S(+) composition produces the substantially pure enantiomeric salt as a greater than 98% ee S(+) pure product. Of course, compositions having smaller amounts of enrichment than the above noted 66% ee S(+) produce final product of less than 84% ee S(+). The relationship between composition of the starting carboxylic acid and composition of the final carboxylic acid is surprisingly linear. The process of this invention provides, in one step, a product that is obtained by the prior art processes mentioned earlier in numerous steps. As such, the process provides a more simplified method of obtaining highly pure enantiomeric salts of the carboxylic acids of formula I than previously available.

The purified salt obtained from the process of the present invention may be further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even a greater extent.

The following examples are for illustration only and is not intended as limiting the invention in any way.

EXAMPLES

General

Optical purities of the starting ibuprofen, the precipitated salt and the mother liquors wre determined by HPLC using a chiral AGP 100-4 column from Advanced Separation Technologies with an eluant of 1% (V/V) isopropanol in water containing potassium dihydrogen phosphate and N,N-dimethyloctylamine.

Enrichment of the Precipitate

EXAMPLE 1

Sodium Salt of Ibuprofen (a) To a stirring solution of 10.3 g (50 mmol) of ibuprofen [optical purity=76% ee]in 100 mL of acetone, 1.0 g (25 mmol) of sodium hydroxide was added and stirred to dissolve. After evaporating most of the solvent, the residue was treated with 100 mL of ether. The precipitate was filtered and washed with ether to isolate 5.4 g of sodium salt of ibuprofen with an optical purity of 100% ee.

(b) Ibuprofen (10.3 g, 50 mmol; optical purity=76% ee) was dissolved in 150 mL of hexane by stirring at room temperature. Sodium hydroxide (1.0 g, 25 mmol) was added to the stirring solution. After about 30 minutes white solids started precipitating. The mixture was stirred at room temperature for 3 hrs. and then cooled in an ice-bath for an hour. It was filtered and washed with hexane. 3.6 g of the sodium salt with an optical purity of >98% ee was obtained.

(c) A solution of ibuprofen (10.3 g, 50 mmol; optical purity=66% ee) in 70 mL of octane was heated to 100° C. 1.5 g (38 mmol) of sodium hydroxide was added to the hot solution. After the pellets dissolved completely, the pale yellow solution was cooled to room temperature and stirred for 2 hrs. The precipitated salt was filtered and washed with ether. Yield of the salt=5.6 g and the optical purity=84% ee.

EXAMPLE 2

Cesium Salt of Ibuprofen

To a solution of 10.3 g (50 mmol) of ibuprofen (optical purity=76% ee) in 100 mL of hexane, 4.0 g (24 mmol) of cesium hydroxide monohydrate was added and stirred. Most of the solids dissolved and 5 mL of acetone was added to get a clear solution. After about 1 hr. of stirring, a white solid started precipitating. Stirring was continued overnight. The precipitate of cesium salt was isolated by filtration. Yield=8.4 g and optical purity=99% ee.

EXAMPLE 3

Lithium Salt of Ibuprofen

To a solution of ibuprofen (10.3 g, 50 mmol; 76% ee) in 100 mL of acetone, 0.6 g (25 mmol) of lithium hydroxide was added and stirred at room temperature. Most of the solvent was evaporated and the residue was triturated with 30 mL of THF. The white precipitate was filtered to isolate 2.9 g of the lithium salt with an optical purity of 96% ee.

EXAMPLE 4

Zinc salt of Ibuprofen

Ibuprofen (10.3 g, 50 mmol; 75% ee) was dissolved in 100 mL of water containing 6.0 g (60 mmol) of triethylamine and heated to about 60° C. An aqueous solution of 1.7 g (12.5 mmol) of zinc chloride in 50 mL of water was added dropwise to the hot solution. After completion of the addition, the mixture was cooled to room temperature; the white precipitate was filtered and washed with acetone and air-dried. Yield of the zinc salt=5.4 g and optical purity=96% ee.

EXAMPLE 5

Copper Salt of Ibuprofen

A solution of a mixture of 10.3 g (50 mmol; 73% ee) of ibuprofen and 6 mL of triethylamine was heated to 60° C. and stirred A solution of copper(II) chloride (1.5 g, 11 mmol) in 50 mL of water was added dropwise to the ibuprofen solution. After the addition, the mixture was cooled to room temperature and the precipitate was filtered. Yield of the copper salt=6.2 g and its optical purity=80% ee.

EXAMPLE 6

Lanthanum Salt of Ibuprofen

To a solution of 10.3 g of ibuprofen (76% ee) and 6 mL of triethylamine in 100 mL of water at 60° C., lanthanum chloride heptahydrate (3.0 g, 8 mmol) in 50 mL of water was added in drops. After the addition, the mixture was cooled to room temperature and the white precipitate was filtered and air-dried to isolate 5.0 g of the lanthanum salt. Optical purity of ibuprofen in the salt=81% ee.

EXAMPLE 7

Racemic α-Methylbenzylamine Salt of Ibuprofen

Ibuprofen (10.5 g, 51 mmol; 77% ee) was dissolved in 100 mL of heptane and heated to about 60° C. and stirred. To this hot solution, 4.5 g (37 mmol) of racemic-α-methylbenzylamine in 25 mL of heptane was added in drops. After completion of addition the mixture was cooled to room temperature. The precipitated salt was filtered and washed with ether and air-dried. Yield of the salt = 1.1 g and optical purity = 96% ee.

Enrichment of the Mother Liquor

EXAMPLE 8

Potassium Salt of Ibuprofen

Ibuprofen (10.3 g, 50 mmol; 76% ee) was dissolved in 100 mL of acetone. Potassium hydroxide pellets (1.5 g; 23 mmol) containing 10–15 % water was added and stirred to dissolve the solids. The solution was then concentrated by evaporating the solvent and the residue was treated with 100 mL of hexane. Precipitated potassium salt of ibuprofen was isolated by filtration. Yield = 3.3 g and optical purity = 63% ee. Optical purity of ibuprofen in the mother liquor was found to be 80% ee.

EXAMPLE 9

Calcium Salt of Ibuprofen

A mixture of 10.3 g (50 mmol; 77% ee) of ibuprofen and 6 mL of triethylamine was dissolved in 100 mL of water and heated to 60° C. A solution of 1.4 g (12.5 mmol) of calcium chloride in 50 mL of water was added in drops to hot solution and stirred. After the addition was complete, the mixture was stirred at 60 C. for 30 minutes and cooled to room temperature. The precipitate was filtered to isolate 4.6 g of calcium salt of ibuprofen with an optical purity of 59% ee. Optical purity of ibuprofen in the mother liquor was found to be 86% ee.

We claim:

1. A process for producing a substantially pure enantiomeric salt of an aryl-substituted aliphatic carboxylic acid having the formula:

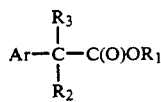

where $R_1$ is hydrogen or alkyl; $R_2$ and $R_3$ are the same or different and are hydrogen alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; which comprises:

(i) reacting said aryl-substituted aliphatic carboxylic acid enriched with one of the enantiomers with an optically inorganic base thereby forming a salt of said aryl-substituted aliphatic carboxylic acid enriched with said enantiomer, said salt having: (a) at least one eutectic point; (b) a composition that is not at the eutectic point; and (c) a eutectic composition that is closer to the racemic composition than is the eutectic composition of said aryl-substituted carboxylic acid.

(ii) treating said salt with an inert solvent;

(iii) separating a salt of the substantially pure enantiomer of the aryl-substituted aliphatic carboxylic acid.

2. The process according to claim 1 wherein said inorganic base is a metal hydroxide, carbonate, bicarbonate or chloride.

3. The process according to claim 2 wherein the metal is from Group I or II of the Periodic Table of Elements.

4. The process according to claim 3 wherein said inorganic base is sodium hydroxide.

5. The process of claim 1 wherein the solvent for said of step (ii) is a inert organic solvent.

6. The process according to claim 1 wherein the ratio of said base is from about 0.2 to about 0.95 mole per mole of enantiomerically enriched aryl-substituted aliphatic carboxylic acid.

7. The process according to claim 6 wherein the ratio is from about 0.4 to about 0.6 made per mole of enantiomerically enriched aryl-substituted aliphatic carboxylic acid.

8. The process of claim 1 wherein said aryl-substituted aliphatic carboxylic acid enriched with one or its enantiomemers is treated with said base at a temperature of from about 25° C. to about 125° C.

9. The process according to claim wherein $R_2$ is hydrogen, $R_3$ is methyl and Ar is phenyl substituted with isobutyl.

10. The process of claim 9 wherein the enantiomerically enriched carboxylic acid is obtained from a diastereomeric crystallization process.

11. The process of claim 9 wherein the enantiomerically enriched carboxylic acid is obtained from a catalyzed kinetic resolution process.

12. The process according to claim 11 wherein said catalyzed kinetic resolution process is carried out with a chemical catalyst.

13. The process according to claim 11 wherein said catalyzed kinetic resolution process is carried out with biological catalyst.

14. The process according to claim wherein said enantiomerically enriched carboxylic acid is obtained from catalyzed asymmetric synthesis.

15. The process according to claim 14 wherein the catalyst is a chemical catalyst.

16. The process according to claim 14 wherein the catalyst is a biological catalyst.

* * * * *